United States Patent [19]

Meyer et al.

[11] Patent Number: 4,798,603
[45] Date of Patent: Jan. 17, 1989

[54] ABSORBENT ARTICLE HAVING A HYDROPHOBIC TRANSPORT LAYER

[75] Inventors: Stephen C. Meyer, Cobb County; Roger L. Lance, Gwinnet County, both of Ga.; Connie L. Hetzler, Winnebago County, Wis.; Cedric A. Dunkerly, II, Outagamie County, Wis.; Thomas H. Roessler; David L. Zenker, both of Winnebago County, Wis.; Michael A. Sciaraffa, Outagamie County, Wis.

[73] Assignee: Kimberly-Clark Corporation, Neenah, Wis.

[21] Appl. No.: 109,784

[22] Filed: Oct. 16, 1987

[51] Int. Cl.$^4$ .............................. A61F 13/16
[52] U.S. Cl. ...................... 604/378; 604/379; 604/383
[58] Field of Search ............... 604/378–385, 604/365–377

[56] References Cited

U.S. PATENT DOCUMENTS

| | | | |
|---|---|---|---|
| 3,592,194 | 7/1971 | Duncan | 128/287 |
| 3,595,235 | 7/1971 | Jespersen | 128/284 |
| 3,665,921 | 5/1972 | Stumpf | 128/287 |
| 3,871,378 | 3/1975 | Duncan et al. | 128/290 |
| 3,927,673 | 12/1975 | Taylor | 128/287 |
| 3,945,386 | 3/1976 | Anczurowski et al. | 128/287 |
| 3,965,906 | 6/1976 | Karami | 128/287 |
| 3,987,792 | 10/1976 | Hernandez et al. | 128/284 |
| 4,014,341 | 3/1977 | Karami | 128/287 |
| 4,041,951 | 8/1977 | Sanford | 128/287 |
| 4,077,410 | 3/1978 | Butterworth et al. | 128/287 |
| 4,232,674 | 11/1980 | Melican | 128/287 |
| 4,259,958 | 4/1981 | Goodbar | 128/287 |
| 4,285,342 | 8/1981 | Mesek | 128/287 |
| 4,304,234 | 12/1981 | Hartman | 128/287 |
| 4,324,247 | 4/1982 | Aziz | 128/287 |
| 4,338,371 | 7/1982 | Dawn et al. | 428/283 |
| 4,372,312 | 2/1983 | Fendler et al. | 128/290 |
| 4,381,611 | 5/1983 | Wishman | 34/9 |
| 4,381,782 | 5/1983 | Mazurak et al. | 604/368 |
| 4,392,861 | 7/1983 | Butterworth et al. | 604/366 |
| 4,405,325 | 9/1983 | Antlfinger et al. | 604/370 |
| 4,413,032 | 11/1983 | Hartmann et al. | 428/288 |
| 4,421,813 | 12/1983 | Athey | 428/195 |
| 4,436,780 | 3/1984 | Hotchkiss et al. | 428/198 |
| 4,480,000 | 10/1984 | Watanabe et al. | 428/284 |
| 4,500,315 | 2/1985 | Pieniak et al. | 604/379 |
| 4,519,798 | 5/1985 | Dinius | 604/358 |
| 4,519,799 | 5/1985 | Sakurai et al. | 604/366 |
| 4,531,945 | 7/1985 | Allison | 604/378 |
| 4,535,020 | 8/1985 | Thomas et al. | 428/131 |
| 4,537,590 | 8/1985 | Pieniak et al. | 604/379 |
| 4,540,414 | 9/1985 | Wishman | 604/378 |
| 4,540,454 | 9/1985 | Pieniak et al. | 156/62.2 |
| 4,550,725 | 11/1985 | Wishman | 128/155 |
| 4,559,051 | 12/1985 | Hanson | 604/385 |
| 4,560,372 | 12/1985 | Pieniak | 604/369 |
| 4,573,988 | 3/1986 | Pieniak et al. | 604/379 |
| 4,578,066 | 3/1986 | O'Connor | 604/366 |
| 4,608,292 | 8/1986 | Lassen | 428/131 |
| 4,623,340 | 11/1986 | Luceri | 604/385 |
| 4,636,209 | 1/1987 | Lassen | 604/378 |
| 4,675,013 | 6/1987 | Ruffo | 604/366 |
| 4,699,619 | 10/1987 | Bernardin | 604/378 |
| 4,704,112 | 11/1987 | Suzuki et al. | 604/378 |

FOREIGN PATENT DOCUMENTS

| | | | |
|---|---|---|---|
| 165807A1 | 12/1985 | European Pat. Off. | |
| 174775 | 3/1986 | European Pat. Off. | |
| 193309 | 9/1986 | European Pat. Off. | 128/287 |
| 3525379 | 1/1987 | Fed. Rep. of Germany | |
| 61-2854 | 1/1986 | Japan | |
| 8500157 | 9/1986 | Japan | |
| 2023068A | 12/1979 | United Kingdom | 128/284 |
| 2055586A | 3/1981 | United Kingdom | |
| 2101038A | 1/1983 | United Kingdom | 128/287 |
| 2145661A | 4/1985 | United Kingdom | |
| 2170108A | 7/1986 | United Kingdom | |

Primary Examiner—John D. Yasko
Attorney, Agent, or Firm—Paul Yee

[57] ABSTRACT

A distinctive absorbent article includes an absorbent body composed of a substantially hydrophilic material which is capable of absorbing a selected liquid. A liquid permeable topsheet layer composed of a substantially hydrophobic material is superposed in facing relation with said absorbent body and has an effective average pore size therein. A liquid permeable transport layer is located between the topsheet layer and the absorbent body, and is composed of a material which is less hydrophilic than the absorbent body and has an effective average pore size therein which is smaller than the pore size of the topsheet layer.

52 Claims, 3 Drawing Sheets

ABSORBENT ARTICLE HAVING A HYDROPHOBIC TRANSPORT LAYER

TECHNICAL FIELD

The present invention pertains to an absorbent article, such as a disposable diaper, feminine care pad, incontinence garment, wound dressings and the like. More particularly, the present invention pertains to an absorbent article which includes a transfer layer configured to increase the rate of liquid absorption by the article and reduce the flowback of absorbed liquid against the skin of the wearer.

BACKGROUND OF THE INVENTION

Conventional absorbent articles typically include one or more paper-thin topsheet layers composed of hydrophobic fibers. The topsheet layers are typically arranged to separate a pad of absorbent material away from the user's body and thereby reduce the amount of wetness contacting the skin. Various types of structures have been employed in an attempt to provide greater isolation from the liquid in the absorbent pad.

European patent application EP No. 0 165 807 AI of T. W. Osborn III published Dec.27, 1985 describes a sanitary napkin which includes an apertured topsheet and a resilient layer underlying the topsheet. The absorbent structure can also include a wicking layer between the apertured topsheet and the resilient layer, an absorbent core underlying the resilient layer, and a moisture barrier located against the outermost side of the absorbent core. A described function of the resilient layer is that it tends to isolate the apertured topsheet from bodily discharges which have already passed through the topsheet and that it serves as a reservoir for bodily discharges.

Various types of diaper structures have employed hydrophilic wicking layers to conduct fluid within an absorbent structure. For example, see U.S. Pat. No. 4,338,371 issued July 6, 1982 to F. Dawn, et al.; U.S. Pat. No. 4,259,958 issued Apr. 7, 1981 to R. Goodbar; and U.K. patent application GB No. 2 170 108 A of L. Bowman, et al. published July 30, 1986.

Other diaper configurations have employed embossed layers configured to provide raised regions that separate the user from the absorbent pad. For example, see U.S. Pat. No. 4,324,247 issued Apr. 13, 1986 to M. Aziz; U.S. Pat. No. 4,041,951 issued Aug. 16, 1977 to L. Sanford; U.S. Pat. No. 3,945,386 issued Mar. 23, 1976 to E. Anczurowski, et al.; and U.S. Pat. No. 4,413,032 issued Nov. 1, 1983 to L. Hartmann, et al.

U.S. Pat. No. 4,480,000 issued Oct. 30, 1984 to I. Watanabe, et al. describes an absorbent article which includes an absorbent core layer and a barrier covering the lateral faces and the underneath face of the absorbent core layer. A web predominantly comprised of a polyester fiber is placed on top of the absorbent core layer, and a nonwoven fabric is wrapped around the structure. The absorbent articles are described as being able to absorb fluid at an enhanced rate and have a feeling of dryness even after such absorption.

U.S. Pat. No. 3,987,792 issued Oct. 26, 1976 to J. Hernandez, et al. describes a disposable diaper comprising, in order, a water-pervious layer; a spongy, resilient and compressible hydrophobic fibrous layer; an absorbent core; and a water-impervious layer. The hydrophobic fibrous layer is pervious to fluids in the uncompressed condition, but is impervious to fluids when compressed. The description indicates that the compressed fibers intermesh to form a seal or barrier.

Conventional absorbent articles, such as those described above, have not been completely satisfactory. The absorbent articles have not been sufficiently able to both rapidly conduct fluid into an absorbent core and also inhibit the flowback and contact of absorbed liquid against the skin of the wearer. In addition, some structures, such as those described in EP No. 0 165 807 A1, have been excessively bulky.

BRIEF DESCRIPTION OF THE INVENTION

The present invention provides a distinctive absorbent article which includes an absorbent body composed of a material capable of absorbing a selected liquid, and a liquid permeable topsheet layer. The topsheet layer has an effective average pore size therein and superposed in facing relation with a first major surface of the absorbent body. A liquid permeable transport layer and is located between the absorbent body and the topsheet layer, and is composed of a material which is less hydrophilic than the absorbent body. The transport layer has an effective average pore size therein which is less than the average pore size of the topsheet layer. In particular aspects of the invention, the transport layer may have a density within the range of about 0.015-0.5 g/cc, and a wet compression recovery value of at least about 65%.

The absorbent article of the invention can advantageously provide flexibility, low bulk, and reduced flowback of liquids out of the absorbent body. As a result, the article of the invention can provide less wetness against the skin and greater comfort to the wearer.

BRIEF DESCRIPTION OF THE DRAWINGS

The invention will be more fully understood and further advantages will become apparent when reference is made to the following detailed description of the invention and the following drawings in which.

DETAILED DESCRIPTION OF THE INVENTION

The following detailed description will be made in the context of a disposable diaper article. It is readily apparent, however, that the absorbent structure of the present invention would also be suitable for other absorbent articles, such as feminine care pads, sanitary napkins, incontinence garments, wound dressings and the like.

Figure 1:
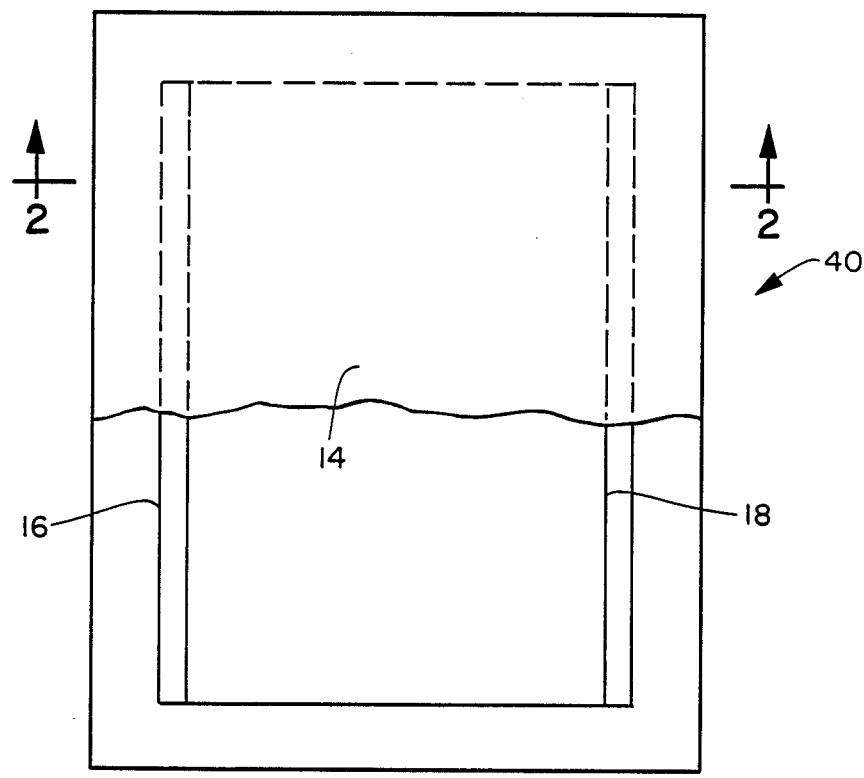
FIG. 1 representatively shows a top plan view of an absorbent article of the invention.
Figure 2:
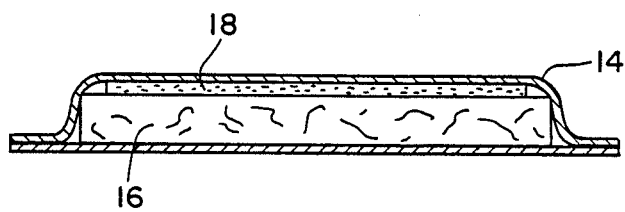
FIG. 2 representatively shows a cross-sectional view taken along line 2—2 of FIG. 1.

With reference to FIG. 1, an absorbent article 40 includes an absorbent body 16 and a liquid permeable topsheet layer 14. The absorbent body is composed of a substantially hydrophilic material capable of absorbing a selected liquid, such as urine and other bodily discharges. The topsheet layer is superposed in facing relation with a first major surface of the absorbent body, and has an effective average pore size therein, which typically is larger than the pore size of the absorbent body. A liquid permeable transport layer 18 is located between absorbent body 16 and topsheet layer 14. The transport layer is composed of a material which is less hydrophilic than the absorbent body material, and may generally be characterized as being substantially hydrophobic. The transport layer has an effective average pore size therein which is greater than the pore size of the immediately adjacent portion of absorbent body 16, but less than the pore size at topsheet 14. In particular aspects of the invention, the transport layer may have a density within the range of about 0.015–0.5 g/cc, and a wet compression recovery value of at least about 65%.

Figure 3:
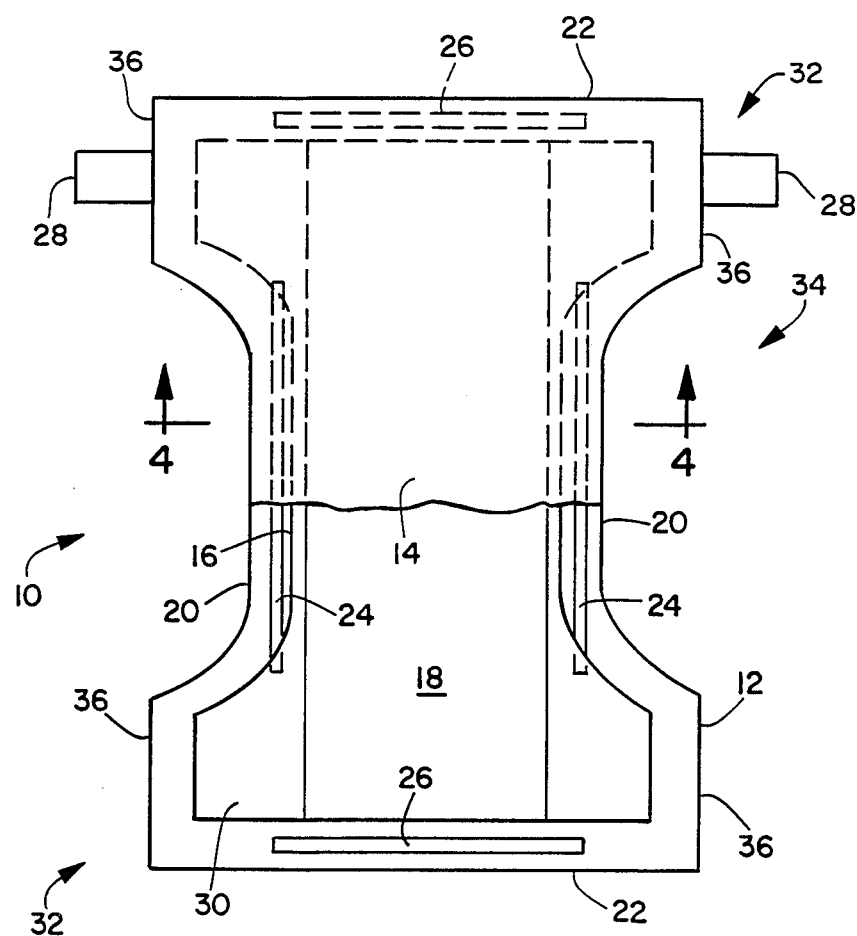
FIG. 3 representatively shows a top plan view of an absorbent diaper article of the invention.

With reference to FIG. 3, an absorbent article, such as disposable diaper article 10, includes a backsheet layer 12 and a substantially liquid permeable topsheet layer 14 superposed in facing relation with the backsheet layer. An absorbent body 16 composed of a substantially hydrophilic material capable of absorbing a selected liquid is located between backsheet layer 12 and topsheet layer 14, and a liquid permeable transport layer 18 composed of a substantially hydrophobic material is located between topsheet 14 and absorbent body 16. The transport layer has a substantially uniform density, and a wet compression recovery value of at least about 65% in the presence of water. In the shown embodiment, backsheet 12 and topsheet 14 are essentially coterminous and extend out past the edges of absorbent body 16 to form marginal edges 20 and 22. The diaper components each have waistband portions 32 interconnected by an intermediate portion 34, and in the illustrated embodiment, the intermediate portion is narrower than the waistband portions. Diaper 10 thus has a generally hourglass or I-shape planform with the waistband portions 32 defining ear sections 36 extending oppositely along the lateral cross-wise direction. Two ear sections at one waistband portion of the diaper include securement means for fastening the diaper on the wearer. In the illustrated embodiment, the securement means are operably connected to the back waistband portion of the diaper and comprise adhesive tape tabs 28. It is readily apparent, however, that various other securement means, such as hooks, snaps, cohesive strips and the like could also be employed. The illustrated embodiment further includes elastic members 24, which are attached to each of the diaper side margins 20 and configured to gather and shirr the legband portions of diaper 10 to form seals or gaskets about the legs of the wearer. In addition, diaper 10 can include waist elastic members 26 secured to one or more end margins 22 to gather and shirr the waistband portions of the diaper. Other embodiments of the invention can include, for example, a generally rectangular-shaped absorbent pad 16, and perforations formed through the side margins of backsheet layer 12. The perforations may, for example, have diameters of up to about 0.020 inch and may be arranged to provide about 100–300 perforations/sq. inch of backsheet area. The perforated area preferably is limited to the portion of the side margins of the backsheet located between the leg elastic member and the terminal side edge of the backsheet, but may cover a greater portion or even all of the area of the backsheet, if desired.

The various components of diaper 10 are assembled together employing conventional techniques. For example, the components may be attached to one another employing thermal or sonic bonds, or mechanical fasteners, such as snaps or clips. Alternatively, the components can be attached with adhesives, such as hot melt pressure-sensitive adhesives. The adhesives can be applied by employing conventional techniques, such as by spraying droplets or filaments of adhesive. In the shown embodiment of the invention, the components are assembled employing a plurality of generally parallel lines of hot melt pressure-sensitive adhesive oriented along the length dimension of the diaper.

In a particular embodiment of the invention, backsheet 12 is composed of a liquid impermeable material, such as a polymer film. For example, backsheet 12 can be composed of a polyolefin film, such as polyethylene or polypropylene. In another embodiment of the invention, backsheet 12 can be composed of a liquid impermeable, but vapor permeable material, such as a breathable, microporous polyethylene film. In yet another embodiment of the invention, the backsheet can be composed of a vapor permeable, nonwoven fibrous material which has been suitably treated to impart a desired degree of liquid impermeability. For example, the backsheet may comprise a nonwoven spunbonded layer which has been completely or partially coated with a polymer film to provide liquid impermeability in particular areas.

Topsheet 14 is typically composed of a liquid permeable, substantially hydrophobic fibrous material, such as a spunbonded web composed of synthetic polymer filaments. Alternatively, topsheet 14 may comprise a meltblown web or a bonded-carded-web composed of synthetic polymer filaments. Suitable synthetic polymers include, for example, polyethylene, polypropylene and polyesters. In a particular aspect of the invention, the polymer filaments have a denier within the range of about 1.5–7, and preferably have a denier within the range of about 1.5–3. The filaments are arranged to form a layer having a basis weight within the range of about 0.6–1.0 oz/yd$^2$ (osy), and preferably a basis weight of about 0.8 osy. In addition, the topsheet layer has a bulk thickness within the range of about 0.008–0.017 in, and preferably a bulk thickness within the range of about 0.010–0.012 in for improved effectiveness. The bulk thickness is measured under a restraining pressure of 0.014 pi. The topsheet has a pore size that readily allows the passage therethrough of liquids, such as urine and other body exudates. A particular aspect of the invention includes a topsheet having an effective average pore size, in terms of equivalent circular diameter (ECD), which is within the range of about 40–110 micrometers, and preferably within the range of about 70–110 micrometers to provide improved effectiveness.

Optionally, the topsheet can be treated with surfactants to adjust its degree of hydrophobicity and wettability, and can also be selectively embossed or apertured with discrete slits or holes extending therethrough. When configured with apertures, the apertures may substantially define the effective pore size of the topsheet. In a particular aspect of the invention, the apertures have an average equivalent diameter within the range of about 160–350 micrometers and preferably have an average diameter of about 250 micrometers to provide improved performance. Thusly configured, the topsheet would again have a pore size which is larger than the pore size of transport layer 18.

Absorbent body 16 typically comprises a pad composed of airlaid cellulosic fibers commonly referred to as wood pulp fluff. Conventional pads can have a density ranging from about 0.05–0.20 g/cc, and are sufficiently flexible to readily conform to the body of the wearer. Absorbent body 16 may also comprise a coform material composed of a mixture of cellulosic fibers and synthetic polymer fibers. For example, the coform material may comprise an airlaid blend of cellulosic fibers and meltblown polyolefin fibers, such as polyethylene and polypropylene fibers. In one aspect of the invention, the fibrous material comprising absorbent body 16 is composed of filaments having a coarseness of about 10–20 mg per 100 m, and preferably having a coarseness within the range of about 10–18 mg per 100 m. The filaments are arranged to form a layer having a basis weight within the range of about 400–1200 g/m$^2$ and preferably a basis weight of about 800 g/m$^2$. In addition, the absorbent body material has a bulk thickness within the range of about 0.17–0.21 in, as measured under a restraining pressure of 0.068 psi.

Absorbent body 16 may also include an effective amount of an inorganic or organic high-absorbency material to enhance the absorptive capacity of the absorbent body. For example, absorbent body 16 can include 5–95 wt % high-absorbency material, and preferably includes about 10–30 wt % of the high-absorbency material to provide more efficient performance. Suitable inorganic high-absorbency materials include, for example, absorbent clays and silica gels. Organic high-absorbency materials can include natural materials, such as agar, pectin, guar gum and peat moss, as well as synthetic materials, such as synthetic hydrogel polymers. Such hydrogel polymers include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. The hydrogel polymers are preferably lightly cross-linked to render the materials substantially water-insoluble. Cross-linking may, for example, be by irradiation or by covalent, ionic, Van der Waals, or hydrogen bonding. Suitable materials are available from various commercial vendors, such as Dow Chemical Company., Celanese Corporation, Allied-Colloid, and Stockhausen. Typically, the high-absorbency material is capable of absorbing at least about 15 times its weight in water, and preferably is capable of absorbing at least about 25–50 times its weight in water.

The high-absorbency material can be distributed or otherwise incorporated into absorbent body 16 employing various techniques. For example, the high-absorbency material can be substantially uniformly distributed in the mass of fibers comprising the absorbent body. The material can also be nonuniformly distributed among the fibers to form, for example, a generally continuous gradient with either an increasing or decreasing concentration of high-absorbency material, as determined by observing the concentration moving from the body-side of absorbent body 16 to the outer-side of the absorbent body. Alternatively, the high-absorbency material can comprise one or more discrete layers or strips selectively segregated from the fibrous material of absorbent body 16.

Absorbent body 16 can optionally include a substantially hydrophilic tissue wrap 30 to help maintain the integrity of the airlaid fibrous structure. The tissue wrap sheet typically comprises an absorbent cellulosic material, such as creped wadding or a high wet-strength tissue. In one aspect of the invention, the tissue wrap generally provides a substantial continuation of the pore size gradient established by transport layer 18. More particularly, wrapsheet 30 is configured to have an effective average pore size which is smaller than the effective pore size of the transport layer. In certain preferred aspects of the invention, the wrapsheet material has an effective pore size in terms of equivalent circular diameter (ECD) which is within the range of about 10–40 micrometers, and preferably an effective pore size within the range of about 15–40 micrometers to provide improved performance In yet another aspect of the invention, wrapsheet 30 is configured to provide a distinctive wicking layer which helps to rapidly distribute liquid into the mass of absorbent fibers comprising the absorbent body. More particularly, the wrapsheet material on one side of the absorbent fibrous mass is bonded to the wrapsheet located on the opposite side of the fibrous mass. The bonds are positioned at discrete, separate regions and extend through the thickness of the fibrous mass. Such a configuration shapes the wrapsheet to form a plurality of individual funnels or quilts which help to direct liquids into the interior of the fibrous mass and provide a more rapid absorption of the liquid. An effective embodiment further includes a plurality of holes or apertures formed at least partially through the thickness of the fibrous mass, and is configured such that the bonding of the oppositely positioned layers of wrapsheet material occurs through these holes or apertures. The apertures limit the amount of intervening fibrous material and allow a more direct bonding between the wrapsheet layers. The bonding can comprise adhesive bonds, sonic bonds, thermal bonds or the like.

In an alternative embodiment of the invention, the absorbent article can include a supplemental transport layer located between absorbent body 16 and backsheet 12 as well as the primary transport layer located between the absorbent body and topsheet 14. The two transport layers can then be operably interconnected to each other through the thickness of the absorbent body at selected points to form a quilted arrangement. The absorbent body may again include a plurality of apertures formed at least partially therethrough to allow a more direct connection between the two transport layers at locations substantially in registry with the apertures, and facilitate the formation of the funnel-like quilts. Suitable mechanisms employed to connect the transport layers can be similar to those previously described with respect to the bonding employed to form the quilted pattern in the wrapsheet layers.

Figure 4:
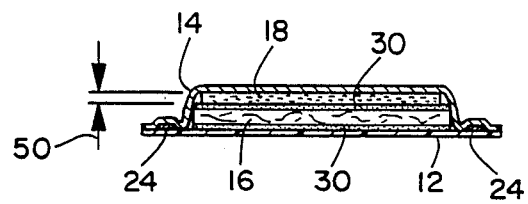
FIG. 4 representatively shows a cross-sectional view taken along line 4—4 of FIG. 3.

With reference to the embodiment of the invention representatively shown in FIGS. 3 and 4, transport layer 18 may be nonwoven fibrous web composed of a substantially hydrophobic material, such as polypropylene, polyethylene, polyester or the like, and also may be composed of a blend of such materials. The transport layer is interposed between topsheet 14 and absorbent body 16, and is configured such that it is capable of attaining a substantially intimate contact with the topsheet and absorbent body. This intimate contact is useful for providing an effective fluid transfer communication from the topsheet to the transport layer and from the transport layer to the absorbent body.

Transport layer 18 has a substantially uniform density in the shown embodiment of the invention, and has an essentially nonlayered configuration, with the composition of the transport layer being substantially uniform throughout its structure. In the illustrated embodiment, transport layer 18 has a density within the range of about 0.015–0.5 g/cc, preferably has a density within the range of about 0.04–0.4 g/cc, and more preferably has a density within the range of about 0.08–0.12 g/cc to provide improved effectiveness. The transport layer also has a fiber denier within the range of about 1.5–15 and preferably has a fiber denier within the range of about 1.5–6 to provide improved effectiveness.

In a particular aspect of the invention, transport layer 18 may be configured with a pore size gradient through the thickness dimension of the transport layer, with the pore sizes increasing in a substantially continuous or discontinuous pattern through the thickness of the layer. For example, the transport layer may comprise a series of stratified zones, wherein each zone has a characteristic pore size and the zones are operably integrated together to form a substantially unitary structure.

For improved performance, transport layer 18, when uncompressed, should be capable of providing an effective, average pore size which is less than that of topsheet 14 but greater than that of at least the immediately adjacent section of absorbent body 16. Such a configuration can advantageously provide a gradient of decreasing pore size as liquid moves from the bodyside of topsheet 14, through the topsheet, through transport layer 18 and into absorbent body 16. In the illustrated embodiment, the gradient occurs in a generally stepwise arrangement. The pore size gradient can advantageously provide a preferential flow direction away from topsheet and toward absorbent body 16, and this preferential flow direction can operate to reduce and restrict flowback of liquids against the wearer's skin.

In a particular embodiment of the invention, transport layer 18 is configured such that the resultant pore size gradient is substantially maintained during the ordinary use of the article by the wearer. In such embodiment, the transport layer is constructed and configured to be capable of being resiliently compressed during ordinary use. Upon such compression, the effective pore size therein remains less than the pore size in the topsheet, but larger than the pore size within the immediately adjacent portion of the absorbent body. When the compression of the transport layer is released, the transport layer can reexpand to provide a larger effective pore size and an increased surge capacity. In a particular preferred embodiment of the invention, the above-described pore size gradient and reexpansion capability of the transport layer are substantially maintained during ordinary use even when the transport layer is wet. For the purposes of the present invention, the ordinary use of the article can be represented by the application of a pressure of about 0.2–0.5 psi (about 1.38–3.45 kPa).

To adjust the performance of the invention, transport layer 18 may be treated with a selected amount of surfactant to increase its initial wettability. When treated with surfactant, however, the transport layer material should still be less hydrophilic than the absorbent body. It has been found that the presence of an effective amount of the surfactant can advantageously increase the rate of movement of liquid into absorbent body during the initial insults or discharges of liquid into the absorbent article. After the initial insult, however, bodily discharges, such as urine, will continue to readily move through the transport layer whether or not the surfactant is present in the transport layer. Accordingly, the surfactant material may be water dispersible and can be allowed to "wash out" of the transport layer, if desired.

In one aspect of the invention, transport layer 18 provides a discrete spacing distance or separation between topsheet 14 and absorbent body 16. The amount of separation generally corresponds to the thickness dimension of the transport layer, and helps to isolate topsheet 14 from absorbent body 16. This isolation can advantageously provide a dryer feel on the body side surface of topsheet 14, and help reduce contact between the wearer's skin and any liquid held within absorbent body 16.

To provide a desired effectiveness, transport layer 18 has an uncompressed dry caliper or bulk thickness dimension 50 within the range of about 0.005–0.2 inches (about 0.013–0.51 cm), when measured under a restraining pressure of 0.014 psi (0.096 kPa). Preferably, the dry thickness of the transport layer is within the range of about 0.01–0.03 inches (about 0.025–0.076 cm) and more preferably is within the range of about 0.012–0.017 inch (about 0.03–0.043 cm) to provide improved effectiveness. If the transport layer is too thick, there can be excessive bulk and excessive retention of liquids within the transport layer. If transport layer 14 is too thin, it may not provide a sufficient amount of separation and spacing between topsheet 14 and absorbent body 16.

To maintain the desired effectiveness of transport layer 18, the transport layer should be capable of sustaining its above-described spacing function even when wetted by urine or other aqueous liquids discharged from the wearer. Accordingly, the wet compression recovery value of transport layer 18 is at least about 65%. Preferably the wet compression recovery value is at least about 80%, and more preferably is at least about 85% to provide improved performance.

The compression recovery value is a measure of the resilience of the material, and is determined by measuring the original thickness ($t_0$) of the transport layer material under a restraining pressure of 0.068 psi (0.47 kPa). The transport layer is then subjected to a compression force of 0.5 psi (3.45 kPa). This compression force is then removed and the recovery thickness ($t_R$) of the material is measured under the original pressure of 0.068 psi (0.47 kPa). The compression recovery value is then determined in accordance with the following formula:

$$\text{compression recovery value} \\ (CRV) = (t_R \div t_0) \times 100\%$$

When the above determination is made employing a dry transport layer, one obtains a dry compression recovery value. When the above determination is made employing a transport layer substantially saturated with distilled water, one obtains a wet compression recovery value. In a particular aspect of the invention, the transport layer has a dry CRB of at least about 65% and a wet CRB of at least about 65%. A preferred embodiment of the invention has a dry CRV and a wet CRV which both are at least about 95%.

As previously discussed, transport layer 18 can be attached or otherwise secured to the assembled absorbent article structure employing conventional techniques, such as thermal bonds, sonic bonds, adhesive bonds and the like. To further improve the effectiveness of the absorbent article, the assembly bonds should be limited to substantially the outer surface regions of transport layer 18 and should not extend a significant distance into the transport layer. Preferably, the absorbent structure is configured such that substantially no bonds extend completely through the thickness dimension of transport layer 18. Bonds extending completely through the transport layer thickness can undesirably provide a low resistance, wicking path for liquid flow and can excessively reduce the effective flowback resistance of the transport layer.

Once the flow of liquid has been initiated into transport layer 18, it is desirable to rapidly conduct liquid through topsheet 14 and minimize any pooling of liquid against the wearer's skin. Ordinarily, absorbent body 16 by itself does not provide sufficient surge capacity. The relatively small pore sizes and capillaries within absorbent body 16 can strongly attract and hold a liquid, but do not collect and draw in the liquid at a sufficiently rapid rate. As a result, an excessive amount of time may be required to gather the liquid through the topsheet and draw it into the absorbent body. During this time, liquid can excessively hydrate the wearer's skin.

To overcome this problem and provide a desired surge capacity, a further aspect of the invention comprises a transport layer having an effective average pore size, in terms of equivalent circular diameter (ECD), which is within the range of about 10–100 micrometers when the transport layer is dry and uncompressed. Preferably, the average pore size of the dry and uncompressed transport layer ranges from about 40–90 micrometers to provide improved effectiveness.

To retain the surge capacity and to better allow the spread and distribution of liquid laterally across the general plane of transport layer 18, the pore size within the transport layer should be substantially maintained even when the transport layer is wetted. Accordingly, a particular aspect of the invention includes a transport layer in which the effective average pore size of the transport layer does not excessively collapse when the transport layer material is wetted with aqueous liquids. Thusly configured, the transport layer can better accommodate repeated insults of discharged liquid, and can more rapidly collect and contain large and sudden surges of the liquid. The liquid can be more effectively held in a region located on the side of topsheet 14 which is opposite from the wearer's skin. In addition, the transport layer can allow a rapid spread of the liquid sideways along its lateral length and width dimensions to expose a larger surface area of absorbent body 16 to the liquid, thereby increasing the potential rate of absorption into the absorbent body.

An example of a suitable transport layer material is a powder-bonded-carded web distributed by H.D.K. of Rogersville, Tenn. The web is composed of KODEL 435, 5.5 denier, polyester fibers bonded with EASTMAN 252 adhesive, which comprises about 16.6 wt % of the web. The web has a bulk density of about 0.1 g/cc, a bulk thickness of about 0.014 in, and a basis weight of about 30 g/yd$^2$.

Another example of a suitable transport layer material is a spunbond web composed of polypropylene, trilobal fibers. The web has a bulk density of about 0.1 g/cc, a bulk thickness of about 0.017 in, and a basis weight of about 35 g/yd$^2$. The web may also include about 0–0.5 wt % of a selected surfactant, such as Triton X-102 distributed by Rohm & Haas Company of Philadelphia, Pennsylvania. Further examples of suitable transport layer materials include spunbond webs composed of polypropylene fibers, which may be round, trilobal or poly-lobal in cross-sectional shape and which may be hollow or solid in structure. Such webs can have a basis weight within the range of about 0.5–2.0 oz/yd$^2$ and a bulk thickness within the range of about 0.010–0.050 inch. Typically the webs are bonded, such as by thermal bonding, over about 3–30% of the web area.

In another aspect of the invention, transport layer 18 when uncompressed, can have an effective average pore size which is larger than the effective average pore size of absorbent body 16 and also larger than the effective average pore size of the topsheet 14. This particular configuration can advantageously provide an increased surge capacity.

The relatively large pore sizes of transport layer 18, however, may undesirably retain excessive amounts of residual liquid therein. The large pores may not effectively pass all discharge liquids into absorbent body 16, and a certain discrete amount of liquid can be held within transport layer 18 even after the liquid insult has ended. To the extent that it is capable, the hydrophilicity and natural capillary action of absorbent body 16 will pull liquid out of the pores of the transport layer. However, some liquids may remain in the pores of the transport layer. This retained liquid within transport layer 18 is not desirable since it can readily be induced to flow back through topsheet 14 and wet the wearer's skin. Additional liquid may be held and retained in topsheet layer 14 since the relative large pore sizes within the transport layer may not provide sufficient capillary force to completely draw the liquid from the topsheet. The retained liquid in the topsheet can further contribute to the amount of wetness felt on the bodyside of the topsheet.

To help remove the retained liquid from transport layer 18 and direct that liquid into absorbent body 16, a particular aspect of the invention includes a transport layer in which the transport layer material is capable of resiliently compressing during normal use. Normal use typically subjects the transport layer to an applied pressure of about 0.2–0.5 psi (1.38–3.45 kPa) over limited regions of the transport layer. Such compressed regions can, for example, occur when an infant is sitting or lying on limited portions of the diaper, and can also occur when the infant is moving. The movements of the infant, for example, can flex and crease the transport layer to produce localized compressions thereof.

In a particularly effective embodiment of the invention, transport layer 18 can resiliently compress during normal use to produce an average pore size which is less than the average pore size of topsheet 14. In addition, to provide improved performance, the transport layer is preferably composed of a material which is capable of resiliently compressing during normal use to provide the desired pore size even after the transport layer has been wetted with distilled water.

The selected compressibility of transport layer 18 allows the effective diameter of the pores of the transport layer to be reversibly decreased. The reduced pore size temporarily reduces the effective capillary diameters (pore size) within the transport layer, and consequently, increases the ability of the transport layer to spread and draw liquids therethrough. As a result, the reversible compressibility of this particular embodiment of transport layer 18 can operably produce an effective pore size gradient, as observed by the liquid moving from topsheet through transport layer and into absorbent body 16. Thus, when subjected to the normal-use pressure of about 0.2–0.5 psi, the transport layer compresses such that it, at least temporarily, provides an effective average pore size which is smaller than the effective average pore size of the topsheet, but larger than the effective average pore size of the absorbent body.

Since absorbent body 16 is hydrophilic and typically configured to have a pore size smaller than that of the compressed transport layer 18, the absorbent body can ordinarily provide a capillary attraction force higher than that of the transport layer. As a result, the natural capillary wicking forces will continually direct liquid in a direction moving from transport layer 18 into absorbent body 16. This directional effect substantially continues until the absorbent body is completely saturated. Since the absorbent body and transport layer closely contact each other, they can operably transfer liquid therebetween. Capillaries within the absorbent body can readily cooperate with the temporarily narrowed capillaries within the compressed transport layer 18, and can thereby direct and conduct residual liquids from the transport layer into the absorbent body. Once the desired transfer of residual liquids from the transport layer has occurred, the transport layer can reexpand in response to the wet resiliency of the transport layer material, and can again establish a relatively large, uncompressed pore size therein. The resilient expansion of the transport layer reestablishes the surge capacity of the transport layer, and reestablishes the isolating separation distance between absorbent body 16 and topsheet 14 and is employed to resist the reverse flowback of liquid from the absorbent body to the topsheet.

An effective embodiment of the invention, for example, include a transport layer comprising a powder-bonded-carded-web composed of polyester fibers manufactured by H.D.K. located in Rogersville, Tenn. The H.D.K. material is composed of 100% polyester hollow fibers having a denier of about 5.5 and a bulk web density of about 0.02 g/cc. The web has a thickness of about 0.065 in (about 0.165 cm), a wet compression recovery value of 81% and a dry compression recovery value of about 88%. The web thickness is determined at a restraining pressure of 0.014 psi.

For the purposes of the present invention, a suitable technique for determining and measuring the effective average pore size of a thin layer of material is by employing a scanning electron microscope. Thin layers, such as those comprising the topsheet, transport layer and tissue wrapsheet, have a thickness of not more than about 0.020 in (about 0.051 cm). As a result of this thinness, the pore size observed at the surface of the material can adequately represent the pore size in the bulk of the material. The surface measurements can be made with a scanning electron microscope employing standard techniques known to persons skilled in the art.

More particularly, a suitable technique involves separating a test sample, which measures at least 6 in by 6 in, into six, substantially randomly chosen pieces each measuring $\frac{1}{2}$ in by 1 in, and then examining a major face surface of each piece. Conceptually, the major surface extends generally along the horizontal x-y plane. Employing conventional techniques, the selected major surface of each piece is vapor coated with a heavy metal, such as gold, to prepare it for analysis with the electron microscope. Two fields-of-view are photographed from each piece to provide a total of twelve photographs. Such a selection of twelve, random photographs provides adequate statistical stability, and can be arranged to form a convenient photo montage for macrostage automation. The choice of magnification for the photographs is not critical for orientation measurements, but a "1% rule" for fiber sizes ratioed to field width is used.

Figure 5:
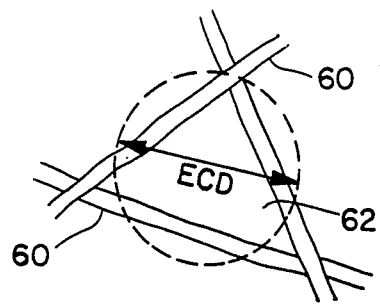
FIG. 5 representatively shows the equivalent circular diameter (ECD) of a pore bounded by three fibers within a nonwoven fibrous web layer.

The photographs are placed on a macroviewer of an image-analysis system, such as a Quantimet 900 series image-analysis system distributed by Cambridge Instruments, Ltd. of Bar Hill, Cambridge CB38EL United Kingdom. The system is set with a magnification sufficient to examine two fields-of-view on each photograph, for a total of 24 fields. Detection (threshholding) is set for the extraction of black pores from amidst the white fiber matrix, and the equipment is programmed in a conventional manner to generate a feature-specific histogram based upon equivalent circular diameter (ECD). The ECD is defined as the diameter of a circle which has substantially the same area as the "pore" space 62 bounded by three or more fibers 60 (FIG. 5). At least several hundred pores, and up to several thousand pores, are then measured and analyzed with all of the individual pore ECDs accumulated into the histogram. Data values produced during the analysis can include the mean, the standard deviation, and selected percent entries in the low-end and high-end regions of the histogram.

The average pore size of the relatively thick absorbent pad is not accurately represented by a two dimension, x-y, view of the pores. By examining the absorbent pad density and absorbent fiber coarseness, however, it can be readily inferred that the average pore size in the absorbent pad is smaller than the average pore sizes of the other layers of the absorbent article. As a result, the absorbent pad can further continue the pore size gradient through the structure of the absorbent article.

Figure 6:
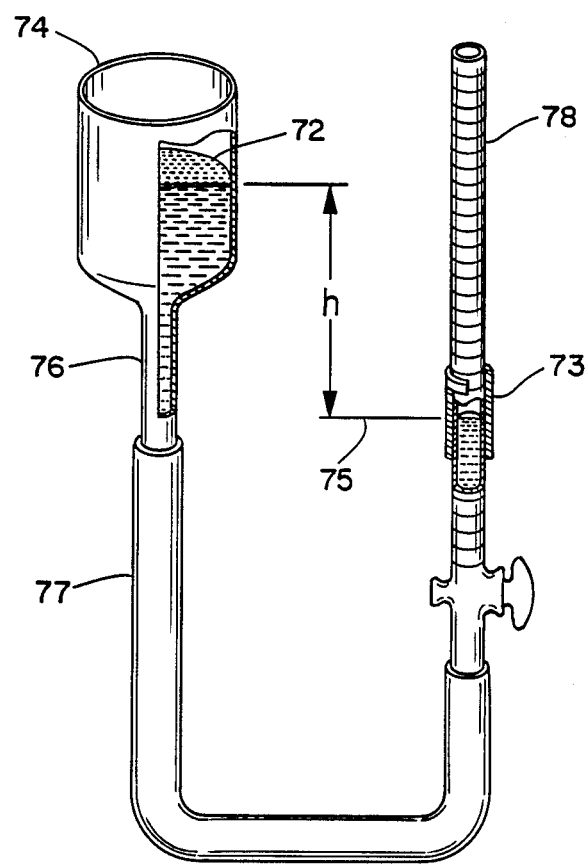
FIG. 6 representatively shows a capillary suction pressure measuring apparatus.

The presence and functionality of a pore gradient structure may also be determined by employing the following Capillary Suction Pressure Test Procedure to analyze the capillary suction pressure of each layer by means of a conventional capillary tension cell apparatus of the type shown in FIG. 6. This apparatus comprises a sintered glass fine frit filter plate 72 which is an integral part of glass funnel 74 connected by glass tube 76 to rubber hose 77 which is in turned connected to buret 78. Funnel 74 is attached to a conventional bench stand along with buret 78, which is disposed alongside funnel 74 as shown in the drawing, and held by clamp 73 which permits manual adjustment. When all connections have been made, the device is filled with fluid so that an uninterrupted air-free column of fluid extends from direct contact with the lower face of filter plate 72 through tubing 77 to the desired level of fluid 75 in buret 78. Fluid level 75 may be set at any predetermined hydrostatic head indicated as value h. This predetermined head is maintained substantially constant while testing any one sample by manually moving buret 78 upwardly in clamp 73 as fluid is absorbed by the sample. The test sample, in the form of a 3 inch diameter disk, is placed on top of filter plate 72 and covered with a perforated nylon disc weighted to supply a light confining pressure of 0.09 psi. Fluid having a surface tension of 32 dynes/cm or less is used to fill the device. An example of such a fluid is simulated urine from Santek Chemicals of Appleton, Wis. having a Neodal surfactant added to lower its surface tension to 32 dynes/cm. As the sample being tested draws fluid through filter plate 72 and fluid level 75 becomes lower, the hydrostatic head is maintained substantially constant by manually adjusting the buret to the predetermined pressure setting. When equilibrium is achieved, i.e., when the fluid column height stops changing, the volume and weight of fluid held in the sample is then recorded.

The absorbent article of the present invention can provide an advantageous combination of a rapid transfer (surge capacity) of liquid away from topsheet 14, and a reduced flowback of absorbed liquids from absorbent body 16 into topsheet 14. A particular aspect of the invention provides absorbent articles which on the average have a surge capacity value of not more than about 20 sec per 80 ml of synthetic urine, and preferably a surge capacity value of not more than about 15 sec per 80 ml of synthetic urine.

A suitable technique for determining the fluid penetration rate and surge capacity value of the absorbent articles is the following Fluid Penetration Rate Test Procedure. This procedure involves taking a whole absorbent article, such as a whole diaper, and removing the elastic members to allow the article to lie flat with the topsheet side of the article facing upward. The article is covered with a test fixture comprising a rectangular acrylic board, which has a 2 inch diameter hold formed through it, and a 2 inch inside diameter, acrylic cylinder which is attached to the board over the hole with the cylinder extending generally perpendicular from the board. The fixture is placed over the test article with the cylinder is centered over a section of the article located 5 inches from the front waistband edge of the article. A funnel is inserted into the cylinder and 80 ml of simulated urine (for example, from Santek Chemicals of Appleton, Wis.) is poured through the funnel into the cylinder. The time for the resultant column of fluid in the cylinder to completely enter the absorbent structure is then measured with a stopwatch. An average fluid penetration rate value can then be determined based upon an average of at least three individual samples.

While the data set forth in the Examples below were generated with the above-described Fluid Penetration Rate Test, it is recognized that the hydrostatic pressure head in the column of fluid may affect the penetration rate value. Accordingly, the test procedure may be modified to limit the rate at which the testing fluid is introduced into the cylinder of the test fixture and minimize the formation of the hydrostatic head.

In a further aspect of the invention, the absorbent article can be characterized by an average flowback value of not more than about 0.5 g, and preferably a flowback value of less than about 0.4 g to provide further improved performance.

A suitable technique for determining the flowback value of an absorbent article is by employing the following Flowback Test Procedure:

For this test, the elastic members are removed from a selected absorbent article, such as a diaper, to allow the article to lie flat, and the weight of the absorbent body component of the article is determined. The article is then wetted with a simulated urine solution having a surface tension of approximately 54–58 dynes. This liquid solution is introduced into the article over an approximately 1 inch diameter area located 5 inches from the front waistband edge of the article, and the addition of liquid is continued until the absorbent component has reached a loading factor of 4.5; that is until the test sample contains 4.5 grams of simulated urine solution per gram of the absorbent body. A uniform pressure loading of 0.5 psi is applied to the test sample for a period of 3 minutes so that the fluid is uniformly distributed throughout the sample. The pressure is momentarily removed, a preweighted sample of absorbent filter paper (James River #120) approximately 4"×12" is inserted lengthwise over the uppermost surface of the topsheet of the absorbent ample, and the 0.5 psi pressure loading is reapplied to the sample for a period of 2 minutes. The filter paper is removed and reweighed, and the amount of fluid absorbed by the filter paper is termed the "flowback" of the sample. The average flowback value is based on an average of at least five individual samples.

The absorbent article of the present invention can also be characterized by the relatively small amounts of liquid retained within the topsheet and transport layer. More particularly, the absorbent article can provide a retained liquid value at the topsheet which is not more than about 0.25 g, and preferably is not more than about 0.2 g for improved performance. In addition, the absorbent article can provide a retained liquid value at the transport layer which is not more than about 0.3 g.

A suitable technique for determining the retained liquid value is by employing the following Fluid Retention Test Procedure:

With this test, a 3.5 inch by 6 inch sample is taken from a selected absorbent article, such as a diaper, and each component layer of the article is preweighed. The sample is wetted with a simulated urine solution having a surface tension of approximately 54–58 dynes, (e.g. available from Santek Chemicals) until the absorbent body component of the article has reached a loading factor of 10; that is until the absorbent component contains 10 grams of simulated urine solution per gram of the absorbent body. The sample is then covered to prevent evaporation and allowed to stand for 15 minutes to reach equilibrium. The topsheet, transport layer, absorbent body and other component layers, if any, can then be individually weighed to determine the amount of liquid retained in each component.

The following examples are provided to give a more detailed understanding of the invention. The particular amounts, proportions, compositions and parameters are meant to be exemplary, and are not intended to specifically limit the scope of the invention.

EXAMPLE 1

An absorbent structure was produced comprising a liquid impermeable backsheet composed of a polyethylene film; a fibrous liquid permeable topsheet; and an absorbent pad sandwiched between the backsheet and topsheet.

The topsheet layer was composed of bilobal polypropylene fibers spunbond to form a web having a bulk thickness of about 0.011 inch and a basis weight of about 0.8 oz/yd$^2$. The resultant spunbonded web had approximately 15% bonded area, and was treated with about 0.3wt % of Triton X-102 surfactant. The average pore size within the topsheet was about 80 micrometers (ECD).

The absorbent pad was composed of about 36 grams of woodpulp fluff and about 5 grams of polyacrylate superabsorbent polymer. The pad had a bulk thickness of approximately 0.24 inch and a bulk density of about 0.15 g/cc, and included a tissue wrap. The tissue wrap layers were composed of a high wet-strength cellulosic tissue having a basis weight of about 22 g/m², and an average pore size of about 32 micrometers (ECD).

EXAMPLE 2

An absorbent structure was produced, comprising a liquid impermeable, polyethylene film backsheet; a fibrous, liquid permeable topsheet; and an absorbent pad sandwiched between the topsheet and backsheet.

The topsheet layer was composed of bilobal polypropylene fibers spunbond to form a web having a bulk thickness of about 0.011 inch and a basis weight of about 0.8 oz/yd². The resultant spunbonded web had approximately 15% bonded area. In addition, the web had an average pore size therein of about 80 micrometers (ECD) and was apertured with holes having an average diameter of about 250 micrometers. The spunbonded web was also treated with about 0.3 wt % of Triton X-102 surfactant.

The absorbent pad was composed of about 36 grams of woodpulp fluff and about 5 grams of polyacrylate superabsorbent polymer. The pad had a bulk thickness of approximately 0.24 inch and a bulk density of about 0.15 g/cc, and included a tissue wrap. The tissue wrap layers were composed of a high wet-strength cellulosic tissue having a basis weight of about 22 g/m², and an average pore size of about 32 micrometers (ECD).

EXAMPLE 3

A transport layer, material obtained from H.D.K., comprised a powder-bonded-carded-web composed of round polyester fibers having a denier of about 6. The fibers were bonded with about 16 wt % of a polyester powder adhesive to form a web having a basis weight of about 30 g/yd², a bulk thickness of about 0.014 inch and a bulk density of approximately 0.10 g/cc. The average pore size within the transport layer was about 52 micrometers (ECD).

EXAMPLE 4

Test samples were prepared comprising a transport layer and an absorbent structure composed of a topsheet and an absorbent pad. The absorbent structure was similar to the structure described in Example 2, differing in the fact that the absorbent pad had a basis weight of about 400 g/m², a bulk density of about 0.1 g/cc, and a bulk thickness of about 0.15 inch. The transport layer had the structure described in Example 3, and was interposed between the topsheet and the absorbent pad. Samples were then tested with the Capillary Suction Pressure Test Procedure described in the present specification at pressures heads (h) of 1 cm and 3 cm. When samples comprising an apertured topsheet, transport layer, and absorbent were tested by this procedure, it was discovered that, as the pore size of each material layer decreased, the ability of that material layer to pull fluid increased, as evidenced by the g/g of fluid retained at equilibrium.

Test results are summarized in Table 1 below.

TABLE 1

| cm of pressure head | Fluid Absorbed (g-Fluid/g) | |
| --- | --- | --- |
| | 1 | 3 |
| Apertured Topsheet | 1.1 | 2.3 |
| Transport Layer | 4.4 | 3.4 |

TABLE 1-continued

| cm of pressure head | Fluid Absorbed (g-Fluid/g) | |
| --- | --- | --- |
| | 1 | 3 |
| *Absorbent | 9.3 | 9.2 |

*Absorbent = 400 g/m² basis weight
0.1 g/cc density
0.15 inches bulk

EXAMPLE 5

Three sets of test samples were prepared. Samples 5A1–5A3 comprised the absorbent structure of Example 1. Samples 5B1–5B3 comprised the absorbent structure of Example 1 combined with the transport layer of Example 3, wherein the transport layer was interposed between the absorbent pad and the topsheet of the absorbent structure. Samples 5C1–5C3 comprised the absorbent structure of Example 2 combined with the transport layer of Example 3, wherein the transport layer was again positioned between the absorbent pad and the topsheet of the absorbent structure. The Fluid Penetration Rate Test Procedure, as described in the present specification, was performed on the samples, and the results are summarized in Table 2 below.

TABLE 2

| Samples | Penetration Rate (sec/80 ml simulated urine) | | |
| --- | --- | --- | --- |
| | 5A | 5B | 5C |
| 1 | 25.3 | 18 | 10.9 |
| 2 | 23.7 | 14.8 | 13.5 |
| 3 | 21.5 | 14.4 | 14.3 |
| Avg. | 23.5 | 15.7 | 12.9 |

The data set forth in Table 2 show that the absorbent structure with a transport layer yields considerable improvement in fluid penetration rate.

EXAMPLE 6

Three sets of test samples were prepared. Samples 6A1–6A5 comprised the absorbent structure of Example 1. Samples 6B1–6B5 comprised the absorbent structure of Example 1 combined with the transport layer of Example 3 such that the transport layer was positioned between the topsheet and the absorbent pad of the absorbent structure. Samples 6C1–6C5 comprised the absorbent structure of Example 2 combined with the transport layer described in Example 3 such that the transport layer was located between the topsheet and absorbent pad of the absorbent structure. The samples were then tested employing the Flowback Test Procedure described in the present specification, and the results are summarized in Table 3 below.

TABLE 3

| Sample | Flowback (grams simulated urine) | | |
| --- | --- | --- | --- |
| | 6A | 6B | 6C |
| 1 | 2.81 | 0.18 | 0.34 |
| 2 | 2.25 | 0.36 | 0.38 |
| 3 | 3.17 | 0.33 | 0.39 |
| 4 | 2.64 | 0.56 | 0.32 |
| 5 | 3.08 | 0.28 | 0.34 |
| Avg. | 2.79 | 0.34 | 0.35 |

From the data set forth in Table 3, it is evident that the transport layer of the present invention yields a distinctive reduction in flowback.

EXAMPLE 7

An absorbent article was constructed, comprising the transport layer of Example 3 interposed between the topsheet and the absorbent pad absorbent structure described in Example 2. A Fluid Retention Test was run in accordance with the procedure described in the present specification, and the results are summarized in Table 4 below.

TABLE 4

|  | Fluid Retain (g-Fluid/g) |
| --- | --- |
| Apertured Topsheet | 0.17 |
| Transport Layer | 0.19 |
| Absorbent | 9 |

Having thus described the invention in rather will be readily apparent to a person of ordinary skill that various changes and modifications can be made without departing from the spirit of the invention. All of such changes and modifications are contemplated as being within the scope of the present invention.

We claim:

1. An absorbent article, comprising:
   an absorbent body composed of a substantially hydrophilic material which is capable of absorbing liquid;
   a liquid permeable topsheet layer superposed in facing relation with said absorbent body and having an effective average pore size therein;
   a liquid permeable transport layer located between said topsheet layer and said absorbent body, and composed of a material which is less hydrophilic than said absorbent body, said transport layer having an effective average pore size therein which is smaller than said topsheet layer pore size.

2. An absorbent article as recited in claim 1, wherein said absorbent body includes an absorbent hydrogel polymer material.

3. An absorbent article as recited in claim 1, wherein said transport layer has a thickness dimension within the range of about 0.013–0.5 cm when uncompressed.

4. An absorbent article as recited in claim 1, wherein said transport Tayer has a thickness dimension within the range of about 0.025–0.076 cm when dry and uncompressed.

5. An absorbent article as recited in claim 1, wherein said transport layer has a thickness dimension within the range of about 0.012–0.017 cm when dry and uncompressed.

6. An absorbent article as recited in claim 1, wherein the effective average pore size of said topsheet is substantially defined by apertures through the topsheet, and wherein said apertures have an average diameter of about 160–350 micrometers.

7. An absorbent article as recited in claim 1, wherein said transport layer comprises a material having an average pore size which ranges from about 10–100 micrometers when said transport layer is dry and uncompressed.

8. An absorbent article as recited in claim 1, wherein said transport layer has a wet compression recovery value of at least about 80%.

9. An absorbent article as recited in claim 1, wherein said transport layer has a wet compression recovery value of at least about 85%.

10. An absorbent article as recited in claim 1, wherein said article has a liquid flowback value of not more than about 0.5 g.

11. An absorbent article as recited in claim 1, wherein said transport layer has a density within the range of about 0.015–0.5 g/cc.

12. An absorbent article as recited in claim 1, wherein said transport layer has a density within the range of about 0.04–0.4 g/cc.

13. An absorbent article as recited in claim 1, wherein said transport layer has a density within the range of about 0.08–0.12 g/cc.

14. An absorbent article as recited in claim 1, wherein said transport layer is composed of a fibrous, nonwoven material.

15. An absorbent article as recited in claim 1, wherein said transport layer comprises a bonded, carded web composed of polyester fibers.

16. An absorbent article as recited in claim 1, wherein said transport layer comprises a powder bonded, carded web composed of polyester hollow fibers.

17. An absorbent article as recited in claim 1, wherein said transport layer is composed of fibers having a denier within the range of about 1.5–15.

18. An absorbent article as recited in claim 1, wherein said transport layer is composed of fibers having a denier within the range of about 1.5–6.

19. An absorbent article as recited in claim 1, wherein said transport layer has a substantially uniform, nonlayered structure through the thickness thereof.

20. An absorbent article as recited in claim 1, wherein said absorbent includes a wrapsheet, composed of a fibrous, substantially hydrophilic material and having an effective average pore size therein which is smaller than said pore size of said transport layer.

21. An absorbent article as recited in claim 20, wherein said wrapsheet has an effective average pore size within the range of about 10–40 micrometers.

22. An absorbent diaper article, comprising:
   a backsheet layer;
   a substantially liquid permeable topsheet layer superposed in facing relation with said backsheet layer, said topsheet layer having an effective average pore size therein;
   an absorbent body which is composed of a substantially hydrophilic material and is capable of absorbing a selected liquid, said absorbent body located between said backsheet and topsheet layers;
   a liquid permeable transport layer located between said topsheet layer and said absorbent body, and composed of a material which is less hydrophilic than said absorbent body, said transport layer having an effective average pore size therein which is smaller than said topsheet pore size.

23. An absorbent article as recited in claim 22, wherein said absorbent body includes an absorbent hydrogel polymer material.

24. An absorbent article as recited in claim 22, wherein said transport layer has a thickness dimension within the range of about 0.013–0.51 cm when uncompressed.

25. An absorbent article as recited in claim 22, wherein said transport layer has a thickness dimension within the range of about 0.025–0.076 cm when dry and uncompressed.

26. An absorbent article as recited in claim 22, wherein said transport layer has a thickness dimension within the range of about 0.012–0.017 cm when dry and uncompressed.

27. An absorbent article as recited in claim 22, wherein the effective average pore size of said topsheet is substantially defined by apertures through the topsheet, and wherein said apertures have an average diameter of about 160–350 micrometers.

28. An absorbent article as recited in claim 22, wherein said transport layer comprises a material having an average pore size which ranges from about 10–100 micrometers when said transport layer is dry and uncompressed.

29. An absorbent article as recited in claim 22, wherein said transport layer has a compression recovery value of at least about 80% when in the presence of said liquid.

30. An absorbent article as recited in claim 22, wherein said transport layer has a wet compression recovery value of at least about 85%.

31. An absorbent article as recited in claim 22, wherein said article has a liquid flowback value of not more than about 0.5 g.

32. An absorbent article as recited in claim 22, wherein said transport layer has a density within the range of about 0.015–0.5 g/cc.

33. An absorbent article as recited in claim 22, wherein said transport layer has a density within the range of about 0.04–0.4 g/cc.

34. An absorbent article as recited in claim 22, wherein said transport layer has a density within the range of about 0.08–0.12 g/cc.

35. An absorbent article as recited in claim 22, wherein said transport layer is composed of a fibrous, nonwoven material.

36. An absorbent article as recited in claim 22, wherein said transport layer comprises a bonded, carded web composed of polyester fibers.

37. An absorbent article as recited in claim 22, wherein said transport layer comprises a powder bonded, carded web composed of polyester hollow fibers.

38. An absorbent article as recited in claim 22, wherein said transport layer is composed of fibers having a denier within the range of about 1.5–15.

39. An absorbent article as recited in claim 22, wherein said transport layer is composed of fibers having a denier within the range of about 1.5–6.

40. An absorbent article as recited in claim 22, wherein said transport layer has a substantially uniform, nonlayered structure through the thickness thereof.

41. An absorbent article as recited in claim 22, wherein said absorbent includes a wrapsheet composed of a fibrous, substantially hydrophilic material and having an effective average pore size therein which is smaller than said pore size of said transport layer.

42. An absorbent article as recited in claim 41, wherein said wrapsheet has an effective average pore size within the range of about 10–40 micrometers.

43. An absorbent article as recited in claim 22, further comprising a supplemental transport layer located between said absorbent body and said topsheet, wherein said transport layer and said supplemental transport layer are operably interconnected to each other through the thickness of said absorbent body at selected points to form an arrangement of funnel-like quilts.

44. An absorbent article as recited in claim 43, wherein said absorbent body includes a plurality of apertures formed at least partially therethrough, and wherein said transport layer and said supplemental transport layer are operably interconnected at locations in registry with said apertures to form said quilts.

45. An absorbent article as recited in claim 22, wherein said transport layer is a nonwoven fibrous web composed of a substantially hydrophobic material.

46. An absorbent article as recited in claim 45, wherein said transport layer is composed of polypropylene, polyethylene, polyester or blends thereof.

47. An absorbent article as recited in claim 40, wherein said transport layer is treated with a selected amount of surfactant to increase its initial wettability.

48. An absorbent article as recited in claim 22, wherein said transport layer is configured with a pore size gradient through a thickness dimension thereof.

49. An absorbent article as recited in claim 48, wherein said transport layer is configured with a pore size gradient through the thickness dimension thereof, with the pore sizes increasing in a substantially continuous pattern through said layer thickness.

50. An absorbent article as recited in claim 49, wherein said transport layer is configured with a pore size gradient with the pore sizes increasing in a substantially discontinuous pattern through said layer thickness.

51. An absorbent article as recited in claim 50, wherein said discontinuous pattern comprises a series of stratified zones.

52. An absorbent article as recited in claim 51, wherein each of said stratified zones has a characteristic pore size and the zones are operably integrated together to form a substantially unitary structure.

* * * * *